United States Patent [19]

Okunaka et al.

[11] Patent Number: 4,643,913
[45] Date of Patent: Feb. 17, 1987

[54] PROCESS FOR PRODUCING SOLAR CELLS

[75] Inventors: Masaaki Okunaka, Fujisawa; Mitsuo Nakatani, Yokohama; Haruhiko Matsuyama, Hiratsuka; Hitoshi Yokono, Fujisawa; Tokio Isogai, Katsuta; Tadashi Saitoh, Tokyo; Kunihiro Matsukuma; Sumiyuki Midorikawa, both of Hitachi; Satoru Suzuki, Yokohama, all of Japan

[73] Assignee: Hitachi, Ltd., Tokyo, Japan

[21] Appl. No.: 687,162

[22] Filed: Dec. 28, 1984

[30] Foreign Application Priority Data

Dec. 28, 1983 [JP] Japan .................. 58-246949

[51] Int. Cl.$^4$ ............................................. H01L 31/18
[52] U.S. Cl. ............................................. 427/75; 29/572; 427/74
[58] Field of Search ................ 427/75, 74; 29/572

[56] References Cited

U.S. PATENT DOCUMENTS 4,328,260  5/1982  Whitehouse ..................... 427/75
4,361,598 11/1982  Yoldas ........................... 427/74
4,463,216  7/1984  Nakano .......................... 29/572

OTHER PUBLICATIONS

Haigh, "Fired Through Printed Contacts on Antireflection Coated Silicon Terrestial Solar Cells", IEEE Photovoltaic Specialists Conference, pp. 360–361 (1976).

Primary Examiner—John D. Smith
Attorney, Agent, or Firm—Antonelli, Terry & Wands

[57] ABSTRACT

A process for producing solar cells which comprises applying a composition for anti-reflection coating formation on one side of a silicon base plate having a p-n junction therein, printing an Ag paste for contact formation on predetermined areas of the coat, and heat-treating the resulting plate at a temperature of 400° to 900° C. to complete anti-reflection coating and a light-receiving side contact, the process being characterized in that the composition for anti-reflection coating formation contains as essential component, (a) at least one member selected from the metal-organic ligand complex compounds represented by the general formula $M(OR_1)_n(L)_{a-n}$ wherein M is a metal selected from Zn, Al, Ga, In, Ti, Zr, Sn, V, Nb, Ta, Mo, and W; $R_1$ is a $C_1$–$C_{18}$ alkyl group; L is an organic ligand which forms an non-hydrolyzable bond with the metal ion; a is the valency of the metal M; and n is an integer satisfying $1 \leq n < a$, and hydrolytic condensation products thereof represented by the general formula $(OR_1)_{n-1}M(L)_{a-n}$—O—$M(OR_1)_{n-1}(L)_{a-n}$, (b) an organotin compound, and (c) a solvent.

26 Claims, 4 Drawing Figures

PROCESS FOR PRODUCING SOLAR CELLS

BACKGROUND OF THE INVENTION

1. Field of the Invention

The present invention relates to a process for producing solar cells, and is directed particularly to a method for the formation of an anti-reflection coating on a silicon substrate having a p-n junction therein.

2. Description of the Prior Art

The conversion efficiency of solar cells is enhanced by covering the light receiving surface of the substrate with an anti-reflection coating to prevent the surface reflection of incident light. This anti-reflection coating is a metal oxide film having a thickness of $\lambda/4$ n ($\lambda$: wavelength of incident light; n: refractive index of metal oxide film), formed on the front face of the substrate. The metal oxide film is formed, for example, by (a) vacuum deposition, (b) sputtering, (c) chemical vapor deposition, or (d) coating and baking of metal complex. Of these methods, (a), (b), and (c) are inferior in productivity because a vacuum system is used for the film formation, and all the methods (a) through (d) require, after formation of an anti-reflection coating on the entire area of the light receiving side of the substrate, local removal of the film by etching, and formation of a collector contact on the stripped area.

To eliminate these drawbacks, there has been proposed a process which comprises coating a p-n junction containing silicon substrate with a metal complex, printing a silver conductive paste on predetermined positions, of the coating, and heat-treating the resulting substrate to complete an anti-reflection coating and a silver contact at the same time, thus achieving the contact of the silver with the silicon substrate (IEEE Photovoltaic Specialists Conference, p.p. 360-361 (1976)).

However, it has been found that the produced solar cells according to this process show high contact resistance between the silver and the silicon substrate and are unsatisfactory in fill factor and conversion efficiency.

SUMMARY OF THE INVENTION

An object of the invention is to provide a process for producing solar cells, which permits the simultaneous formation of an anti-reflection coating and a collector contact by printing and gives a low contact resistance between the silver and the silicon substrate.

BRIEF DESCRIPTION OF THE DRAWING

The FIGURE attached hereto is a flow diagram of solar cell production according to the process of the invention.

DETAILED DESCRIPTION OF THE PREFERRED EMBODIMENTS

Figure 1A:
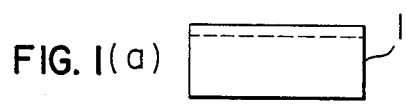
Figure 1B:
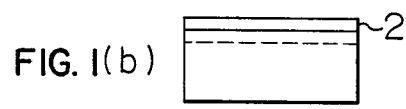
Figure 1C:
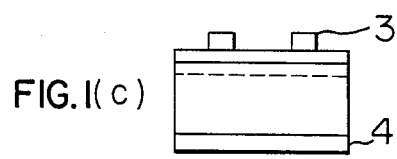
Figure 1D:
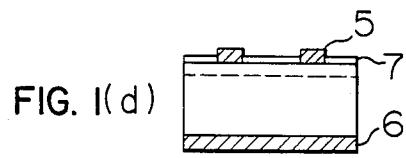

The above object of the invention is achieved by coating a p-n junction-containing silicon substrate with a composition containing at least one alkoxyl-ligand-containing metal complex, at least one organotin compound, and solvent as essential components, drying the coating if necessary, printing a silver conductive paste on predetermined sites, drying the print if necessary, and heat-treating the resulting substrate at a temperature of 400° to 900° C.

The metal alkoxide complex having an alkoxyl group as ligand is represented by the general formula $M(OR_1)_n$, wherein M is a metal ion and $R_1$ is a $C_1$-$C_{18}$ alkyl group ($OR_1$ is a $C_1$-$C_{18}$ alkoxyl group). This complex is readily hydrolyzed by reaction with moisture present in air, as shown in the following equation (1), thereby coating films of this complex being hardened.

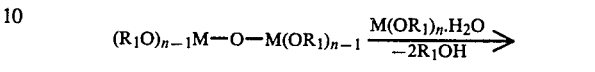

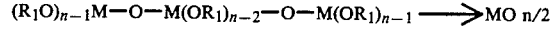

However, the reaction of equation (1) proceeds to excess, resulting in a too hard coating. When such an excessively hardened coating and a silver paste printed thereon are baked simultaneously, the silver will hardly penetrate the coating resulting from the hydrolysis of $M(OR_1)_n$. In consequence, it has been found that the resulting solar cell has no substantial contact of the silver with the silicon substrate.

To control the hydrolysis of equation (1), a part of the alkoxyl groups of the metal complex was replaced by an organic ligand which forms a non-hydrolyzable bond with the metal.

For this ligand there are suited β-diketone anions, carboxylate anions, and dicarboxylate anions represented by the following general formulae (2), (3), and (4), respectively.

In these formulae, $R_2$, $R_3$, and $R_4$ represent $C_1$-$C_{18}$ alkyl groups and $R_5$ represents a group or a $C_1$-$C_{18}$ alkyl group.

Suitable β-diketonate anions represented by formula (2) include, for example, $CH_3CO^{\ominus}CHCOCH_3$, $CH_3CO^{\ominus}CHCOC_4H_9$, and $CH_3CO^{\ominus}CHCOOCH_3$. Suitable carboxylate anions represented by formula (3) include, for example, $CH_3COO^{\ominus}$, $C_3H_7COO^{\ominus}$, $C_2H_5COOCH=CHCOO^{\ominus}$, and $CH_3CH(OH)CH_2COO^{\ominus}$. Suitable dicarboxylate anions represented by formula (4) include, for example, $^{\ominus}OOCCH=C(CH_3)COO^{\ominus}$.

The compound resulting from the metal complex of formula (1) by the partial replacement of the alkoxyl groups with the above ligand is represented by the general formula

wherein M is a metal ion such as Zn, Al, Ga, In, Ti, Zr, Sn, V, Nb, Ta, Mo, or W ion; $R_1$ is a $C_1$-$C_{18}$ alkyl group, L is an organic ligand which forms a non-hydrolyzable bond with the metal ion and more specifically is represented by formulae (2), (3), or (4) above; a is the valency of M; and n is an integer satisfying $1 \leq n < a$.

Suitable examples of the metal complex of formula (5) are $Ti(OC_3H_7)_2(CH_3COCHCOCH_3)_2$, $Al(OC_3H_7)_2(OCOC_3H_7)$, $Zr(OC_4H_9)_3(OCOC_7H_{15})$, $Ta(OC_2H_5)_3(C_2H_5COCHCOOCH_3)_2$. Of these compounds, $Ti(OC_3H_7)_2(CH_3COCHCOCH_3)_2$ is preferred.

Hydrolytic condensation products of the compound represented by formula (5) can also be used. These condensation products are represented by the general formula $$(OR_1)_{n-1}M(L)_{a-n}-O-M(OR_1)_{n-1}(L)_{a-n} \quad (6)$$

wherein M, $R_1$, L, a, and n are the same as in formula (5). A typical example of the comounds represented by formula (6) is the compound having the following structure:

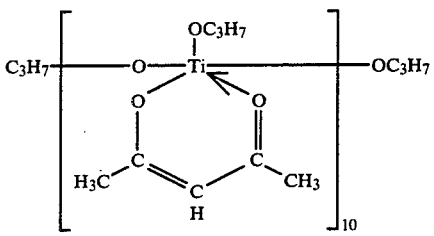

However, the contact resistance was as high as about 0.3 $\Omega cm^2$ as a result of preparing solar cells by forming coats from compounds represented by formula (5) or (6), and printing a contact pattern thereon with a silver conductive paste, followed by the heat-treatment thereof.

But it has been found that this contact resistance can be lowered by using at least one member selected from the compounds represented by formula (5) or (6) and at least one member selected from the organotin compounds represented by the following general formulae (7)–(13).

$$(R_6)Sn(O)(L) \quad (7)$$

$$(R_6)_2SnX(L) \quad (8)$$

$$(R_6)SnX(L)_2 \quad (9)$$

$$(R_6)_3SnL \quad (10)$$

$$(R_6)_3SnX \quad (11)$$

$$(R_6)_2Sn(L)_2 \quad (12)$$

$$(R_6)_3SnSn(R_6)_3 \quad (13)$$

In formulae (7)–(13), $R_6$ is a $C_1$–$C_{18}$ alkyl group, L is a β-diketonate anion represented by formula (2), a carboxylate anion represented by formula (3), or ½ of a dicarboxylate anion represented by formula (4), and X is a hydroxide ion, halide ion, or nitrate ion.

Typical examples of the organotin compounds are as follows: $C_4H_9SnO(CH_3COCHCOCH_3)$, $(C_4H_9)_2Sn(OH)(OCOC_7H_{15})$, $(C_4H_9)_2SnCl(CH_3COCHCOOC_3H_7)$, $(C_4H_9)_2Sn(NO_3)(OCOC_7H_{15})$, $(CH_3)_2Sn(OH)(NO_3)$, $C_4H_9Sn(NO_3)(CH_3COCHCOC_7H_{15})_2$, $(CH_3)_3Sn(CH_3COCHCOCH_3)$, $(CH_3)_2Sn(OCOCH=CHCOO)$, $(C_4H_9)_2Sn(OCOCH=CHCOOC_2H_5)_2$, and $(CH_3)_3SnSn(CH_3)_3$.

In particular, the compounds of formulae (7)–(9) are preferred, because they give finer and tougher films.

Methods for synthesizing these organotin compounds are briefly illustrated below by showing equations of applicable reactions.

Compounds of formula (7), $R_6Sn(O)(L)$:

$$C_4H_9Sn(O)(OH) + CH_3COCH_2COCH_2 \longrightarrow$$

$$C_4H_9Sn(O)(CH_3COCHCOCH_3) + H_2O$$

$$CH_3Sn(O)(OH) + C_7H_{15}COOH \longrightarrow$$

$$CH_3Sn(O)(OCOC_7H_{15}) + H_2O$$

Compounds of formula (8), $(R_6)_2SnX(L)$:

$$(C_4H_9)_2Sn(O) + CH_3COCH_2COOC_3H_7 \longrightarrow$$

$$(C_4H_9)_2Sn(OH)(CH_3COCHCOOC_3H_7)$$

$$(CH_3)_2Sn(O) + C_3H_7COOH \longrightarrow (CH_3)_2Sn(OH)(OCOC_3H_7)$$

Compounds of formula (9), $(R_6)SnX(L)_2$:

$$C_4H_9Sn(O)(OH) + 2CH_3COCH_2COCH_3 \longrightarrow$$

$$C_4H_9Sn(OH)(CH_3COCHCOCH_3)_2 + H_2O$$

$$CH_3Sn(O)(OH) + 2C_7H_{15}COOH \longrightarrow$$

$$CH_3Sn(OH)(OCOC_7H_{15})_2 + H_2O$$

It is also possible that, in lieu of using an isolated organotin compound represented by the formula $(R_6)Sn(O)(L)$, $(R_6)_2SnX(L)$, or $(R_6)SnX(L)_2$, the resulting mixture of the reaction of a compound of the formula $(R_6)Sn(OH)$ or $(R_6)_2Sn(O)$ with a β-diketone or with a carboxylic acid in a solvent is mixed as such with the metal alkoxide complex of formula (5), $M(OR_1)_n(L)_{a-n}$, or with the hydrolytic condensation product thereof, and the resulting solution is used to form the anti-reflection coating.

Thus, the composition used in the invention to form the anti-reflection coating contains at least one member selected from the compounds of formulae (5) and (6), at least one member selected from the organotin compounds of formulae (7)–(13), and a solvent, as essential components.

Suitable mixing ratios of at least one member selected from the compounds of formulae (5) and (6) to at least one member selected from the organotin compounds of formulae (7)–(13) are from 1:0.05 to 1:3.0 by mole. If the proportion of the organotin compound is less than 0.05, the contact resistance lowering effect will be poor, and if the proportion is more than 3.0, the hardness of the resulting film will be insufficient to print the silver conductive paste without marring the film.

Suitable mixing ratios of the sum of at least one member selected from the compounds of formulae (5) and (6) and at least one member selected from the compounds of formulae (7)–(13) to the solvent are from 5:95 to 50:50 by weight. If the proportion of the solvent is more than 95% by weight, the resulting coat will be too thin, and if less than 50% by weight, the composition will be too viscous and difficult to apply. Solvent proportions of 60 to 80% by weight give compositions of best workability.

Any solvent may be used in the invention that dissolves the compound of $M(OR_1)_n(L)_{a-n}$ or the hydrolytic condensation product thereof and the organotin compound. But preferred solvents are alcohols such as ethanol and isopropanol and ethylene glycol monoalkyl ethers, which facilitate the formation of uniform coats. Two or more of these solvents may be used in combination.

The application of the composition to form the anti-reflection coating on the substrate is accomplished by spinner coating, roll coating, dipping, spray, screen printing, or some other methods. In case of screen printing, a thickener such as nitrocellulose, poly(methyl methacrylate), or the like may be added to the composition for anti-reflection coating formation to adjust the viscosity to a suitable level for screen printing.

The Ag paste for contact formation is desired to contain an Ag powder as a main component and a powder of Ti, Mg or Ni and a lead borosilicate glass frit as auxiliary components.

The heat treatment of the coats is desirably carried out at a temperature of 400° to 900° C. Temperatures lower than 400° C. for the treatment will result in insufficient decomposition of organic components in the coating film and in the Ag paste, while temperatures higher than 900° C. result in excessive diffusion of Ag into Si and this tends to cause the leakage.

The invention is illustrated in more detail with reference to the following examples.

EXAMPLE 1

An n+ layer (resistivity ca. $1.5 \times 10^{-3}$ $\Omega$cm) of 0.3–0.5 $\mu$m in depth was formed by the ion implantation method in one side of a p-type silicon substrate 1 (a circular wafer of 3 inches in diameter having a resistivity of 1–5 $\Omega$cm), and a p+ layer of 1–2 $\mu$m in depth was formed by the Al diffusion method in the opposite side of the substrate. Such silicon substrates were used as junction forming silicon substrates for solar cells.

Compositions shown in Table 1 were prepared as coating materials for anti-reflection coatings.

These compositions were applied severally on the n+ layer sides of the silicon substrates by spinner coating. The revolution speed and period were about 3,000 rpm and 60 seconds, respectively. Then, the coatings were 2 dried at about 100° C. for 10 minutes each.

An Ag paste for contact formation was prepared in the following way: A viscous solution of ethyl cellulose (10 parts by weight) in $\alpha$-terpineol (90 parts by weight) was added to a mixture of an Ag powder (10 g) of not greater than 1 $\mu$m in particle size, a Ti powder (1 g) as surface-treated for stabilization, and a PbO—B$_2$O$_3$—SiO$_2$ type glass frit (0.5 g) with thorough stirring, giving the intended paste having a viscosity of about 200 poises (shear rate 100/sec.).

This paste was applied by screen printing on the anti-reflection coating covering the n+ layer of each silicon substrate to form a comb-like pattern 3 and further another pattern 4 on the p+ layer of each substrate to cover the entire surface. The applied paste was dried at 150° C. for 10 minutes. Then, the resulting substrates were baked at 600° C. for 10 minutes in an atmosphere of nitrogen containing 50 ppm oxygen to form the baked patterns, 5, 6 and 7 corresponding to pattern 3, pattern 4 and coating 2, respectively.

The thus prepared solar cells were examined for the current-voltage property (I-V property), short-circuit current density, open voltage, fill factor, and conversion efficiency.

The contact resistance between the Ag and the n+ layer was also measured. Any of the cells showed a short circuit current density of about 28 mA/cm$^2$ and an open voltage of about 0.59 V.

As can be seen from Table 1, the compositions of sample Nos. 1–17 gave characteristics as good as contact resistance values of 0.03–0.04 $\Omega$cm$^2$, fill factor values of 0.78–0.81, and conversion efficiencies of 13.3–13.6%, being much improved as compared with those obtained by using known compositions of sample Nos. 18–21. Sample Nos. 6–16, viz. solar cells prepared by using organotin compounds of the formula (R$_6$)Sn(O)(L) or (R$_6$)$_2$Sn(X)(L) were particularly superior in the fineness in texture of the formed anti-reflection coating.

TABLE 1

| Sample No. | Alkoxyl-containing metal complex (A) (parts by wt.) | |
|---|---|---|
| 1 | Ti(OC$_3$H$_7$)$_2$(CH$_3$COCHCOCH$_3$)$_2$ | (40) |
| 2 | | |
| 3 | | |
| 4 | | |
| 5 | | |
| 6 | | |
| 7 | | |
| 8 | | |
| 9 | | |
| 10 | | |
| 11 | | |
| 12 | | |
| 13 | Al(OC$_3$H$_7$)$_2$(OCOC$_3$H$_7$) | (30) |
| 14 | Zr(OC$_4$H$_9$)$_3$(OCOC$_7$H$_{15}$) | (50) |
| 15 | Ta(OC$_2$H$_5$)$_3$(C$_2$H$_5$COCHCOOCH$_3$)$_2$ | (50) |
| 16 | [complex structure shown] | (50) |

$$\left[ C_3H_7-O-\underset{\underset{\underset{CH_3}{C}=CH}{\overset{O}{|}}}{\overset{\overset{OC_3H_7}{|}}{Ti}}\underset{\underset{CH_3}{C}}{\overset{O}{\diagdown}}-OC_3H_7 \right]_{10}$$

| Sample No. | Alkoxyl-containing metal complex (A) (parts by wt.) | |
|---|---|---|
| 17 | Ti(OC$_3$H$_7$)$_2$(CH$_3$COCHCOCH$_3$)$_2$ | (20) |
| | Al(OC$_3$H$_7$)$_2$(OCOC$_3$H$_7$) | (15) |
| 18 | Ti(OC$_3$H$_7$)$_2$(CH$_3$COCHCOCH$_3$)$_2$ | (40) |
| 19 | Al(OC$_3$H$_7$)$_2$(OCOC$_3$H$_7$) | (30) |
| 20 | Zr(OC$_4$H$_9$)$_3$(OCOC$_7$H$_{15}$) | (50) |
| 21 | Ta(OC$_2$H$_5$)$_3$(C$_2$H$_5$COCHCOOCH$_3$)$_2$ | (50) |

| Sample No. | Organotin compound (parts by wt.) | | Molar ratio $\left(\dfrac{B}{A}\right)$ |
|---|---|---|---|
| 1 | (C$_4$H$_9$)$_3$SnCl | (18) | 0.50 |
| 2 | (C$_4$H$_9$)$_3$Sn(OCOC$_3$H$_7$) | (21) | 0.51 |
| 3 | (CH$_3$)$_2$Sn(OCOCH=CHCOOC$_2$H$_5$)$_2$ | (24) | 0.50 |
| 4 | (CH$_3$)$_2$SnCl$_2$ | (12) | 0.55 |
| 5 | (CH$_3$)$_3$Sn(CH$_3$COCHCOCH$_3$) | (14) | 0.48 |
| 6 | (CH$_3$)$_2$Sn(OH)(NO$_3$) | (13) | 0.52 |
| 7 | CH$_3$Sn(O)(CH$_3$COCHCOCH$_3$) | (14) | 0.51 |
| 8 | C$_3$H$_7$Sn(O)(OCOC$_7$H$_{15}$) | (18) | 0.51 |
| 9 | (CH$_3$)$_2$Sn(OH)(CH$_3$COCHCOCH$_3$) | (15) | 0.52 |
| 10 | (C$_4$H$_9$)$_2$Sn(OH)(C$_3$H$_7$COCHCOOCH$_3$) | (21) | 0.49 |
| 11 | (C$_4$H$_9$)$_2$Sn(OH)(OCOC$_7$H$_{15}$) | (22) | 0.51 |
| 12 | | | 0.50 |
| 13 | | | 0.27 |
| 14 | | | 0.50 |
| 15 | | | 0.63 |
| 16 | C$_4$H$_9$Sn(O)(CH$_3$COCHCOCH$_3$) | (16) | 0.26 |
| 17 | (CH$_3$)$_2$Sn(OH)(NO$_3$) | (10) | — |
| | C$_3$H$_7$Sn(O)(OCOC$_7$H$_{15}$) | (5) | 0.38 |
| 18 | None | | — |
| 19 | | | |
| 20 | | | |

TABLE 1-continued

| Sample No. | Contact resistance ($\Omega$ cm$^2$) | Fill factor | Conversion efficiency (%) |
| --- | --- | --- | --- |
| 1 | 0.03 | 0.80 | 13.5 |
| 2 | 0.04 | 0.79 | 13.3 |
| 3 | 0.03 | 0.81 | 13.6 |
| 4 | 0.03 | 0.81 | 13.6 |
| 5 | 0.03 | 0.80 | 13.5 |
| 6 | 0.04 | 0.80 | 13.5 |
| 7 | 0.03 | 0.81 | 13.6 |
| 8 | 0.03 | 0.81 | 13.6 |
| 9 | 0.03 | 0.80 | 13.5 |
| 10 | 0.04 | 0.78 | 13.3 |
| 11 | 0.03 | 0.81 | 13.6 |
| 12 | 0.03 | 0.81 | 13.6 |
| 13 | 0.03 | 0.81 | 13.6 |
| 14 | 0.03 | 0.80 | 13.5 |
| 15 | 0.03 | 0.81 | 13.6 |
| 16 | 0.03 | 0.81 | 13.6 |
| 17 | 0.03 | 0.80 | 13.5 |
| 18 | 0.31 | 0.49 | 8.6 |
| 19 | 0.30 | 0.47 | 8.3 |
| 20 | 0.38 | 0.53 | 8.9 |
| 21 | 0.35 | 0.51 | 8.7 |

Note:
Ethylene glycol monoethyl ether (100 parts by wt.) was used as solvent.

EXAMPLE 2

Compositions shown in Table 2 were prepared from Ti(OC$_3$H$_7$)$_2$(CH$_3$COCHCOCH$_3$)$_2$, C$_4$H$_9$Sn(O)(CH$_3$COCHCOCH$_3$), and ethylene glycol monoethyl ether. Using these compositions, solar cells were made in the same manner as in Example 1. The characteristic values of these cells are shown in Table 2.

TABLE 2

| Sample No. | Mixing proportion of Ti(OC$_3$H$_7$)$_2$—(CH$_3$COCHCOCH$_3$)$_2$ (A) (parts by wt.) | Mixing proportion of C$_4$H$_9$Sn(O)—(CH$_3$COCHCOCH$_3$) (B) (parts by wt.) | Marring of anti-reflection coating | Molar ratio (B/A) | Contact resistance ($\Omega$cm$^2$) | Fill factor | Conversion efficiency |
| --- | --- | --- | --- | --- | --- | --- | --- |
| 22 | (40) | (0.3) | None | 0.01 | 0.20 | 0.55 | 9.8 |
| 23 | (40) | (1.0) | " | 0.03 | 0.11 | 0.60 | 10.8 |
| 24 | (40) | (1.6) | " | 0.05 | 0.03 | 0.81 | 13.6 |
| 25 | (40) | (6.4) | " | 0.2 | 0.03 | 0.80 | 13.5 |
| 26 | (40) | | " | 1 | 0.03 | 0.81 | 13.6 |
| 27 | (40) | (96) | " | 3 | 0.03 | 0.80 | 13.5 |
| 28 | (40) | (128) | " | 4 | 0.03 | 0.80 | 13.5 |

Note:
Ethylene glycol monoethyl ether (100 parts by wt.) was used as solvent.

From Table 2 it can be seen that the contact resistance becomes saturated when the molar ratio of C$_4$H$_9$Sn(O)(CH$_3$COCHCOCH$_3$) to Ti(OC$_3$H$_7$)$_2$(CH$_3$COCHCOCH$_3$)$_2$ is lower than 0.05. On the contrary, when this ratio was raised over 3.0, a mark of the screen printing plate was observed on the anti-reflection coating with a microscope.

EXAMPLE 3

A composition was prepared from Ti(OC$_3$H$_7$)$_2$(CH$_3$COCHCOCH$_3$)$_2$ (40 parts by weight), C$_4$H$_9$Sn(O)(CH$_3$COCHCOCH$_3$)$_2$ (32 parts by weight), and ethylene glycol monoethyl ether (30 parts by weight), and applied on a silicon substrate. But no uniform coat could be obtained even at a revolution speed as high as 8,000 rpm, since the composition was too viscous.

EXAMPLE 4

A composition was prepared from Ti(OC$_3$H$_7$)$_2$(CH$_3$COCHCOCH$_3$)$_2$ (40 parts by weight), C$_4$H$_9$Sn(O)(CH$_3$COCHCOCH$_3$) (32 parts by weight), and ethylene glycol monoethyl ether (1300 parts by weight), and applied on a silicon substrate. But no anti-reflection coating having a necessary thickness of 700 Å or more could be obtained even at a revolution speed as low as 500 rpm.

What is claimed is:

1. A process for producing solar cells, which comprises applying a composition for anti-reflection coating formation on one side of a silicon substrate which has a p-n junction therein, printing an Ag paste for contact formation or predetermined areas of the coating, and heat-treating the resulting plate at a temperature of 400° to 900° C. to complete an anti-reflection coating and a light-receiving side contact, the composition for anti-reflection coating formation containing as essential components, (a) at least one member selected from the group consisting of organic-ligand-containing metal complex compounds represented by the general formula $$M(OR_1)_n(L)_{a-n} \tag{5}$$

wherein M is a metal selected from Zn, Al, Ga, In, Ti, Zr, Sn, V, Nb, Ta, Mo and W; OR$_1$ is an alkoxyl group; R$_1$ is a C$_1$–C$_{18}$ alkyl group; L is an organic ligand which forms a non-hydrolyzable bond with the metal ion; a is the valency of the metal M; and n is an integer satisfying $1 \leq n < a$, and hydrolytic condensation products of the compounds of formula (5), said products being represented by the general formula $$(OR_1)_{n-1}M(L)_{a-n}O-M(OR_1)_{n-1}(L)_{a-n} \tag{6}$$

wherein M, OR$_1$, L, a, and n are as defined above, (b) at least one organotin compound, and (c) a solvent.

2. The process of claim 1, wherein the organic ligand L is a β-diketonate anion represented by the general formula $$R_2CO^{\ominus}CHCOR_3 \tag{2}$$

wherein R$_2$ and R$_3$ are C$_1$–C$_{18}$ alkyl groups.

3. The process of claim 1, wherein the organic ligand L is a carboxylate anion represented by the general formula $$R_4COO^{\ominus} \tag{3}$$

wherein $R_4$ is a $C_1$-$C_{18}$ alkyl group.

4. The process of claim 1, wherein the organic ligand L is a dicarboxylate anion represented by the general formula $$^\ominus OOCR_5COO^\ominus \quad (4)$$

wherein $R_5$ is a $C_1$-$C_{18}$ alkyl group or a $C_2$-$C_{10}$ alkylene group.

5. The process of claim 2, wherein the β-diketonate anion is $CH_3CO^\ominus CHCOCH_3$.

6. The process of claim 3, wherein the carboxylate anion is $CH_3COO^\ominus$, $C_3H_7COO^\ominus$, or $C_3H_7COO^\ominus$.

7. The process of claim 3, wherein the dicarboxylate anion is $^\ominus OOCH=C(CH_3)COO^\ominus$.

8. The process of claim 1, wherein the metal complex compound of formula (5) is $Ti(OC_3H_7)_2(CH_3COCHCOCH_3)_2$, $Al(OC_3H_7)_2(OCOC_3H_7)$, $Zr(OC_4H_9)_3(OCOC_9H_{15})$, or $Ta(OC_2H_5)_3(C_2H_5COCHCOOCH_3)_2$.

9. The process of claim 1, wherein the hydrolytic condensation product has the structure

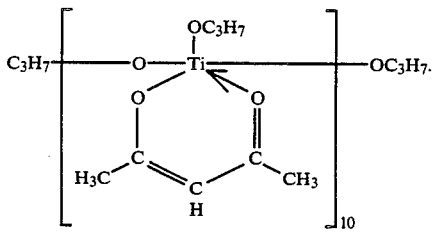

10. The process of claim 1, wherein the organotin compound is at least one member selected from the compounds represented by the general formula $(R_6)Sn(O)(L)$     (7)

$(R_6)_2SnX(L)$     (8)

$(R_6)SnX(L)_2$     (9)

$(R_6)_3Sn(L)$     (10)

$(R_6)_3SnX$     (11)

$(R_6)_2Sn(L)_2$     (12)

or $(R_6)_3SnSn(R_6)_3$     (13)

wherein $R_6$ is a $C_1$-$C_{18}$ alkyl group, L is an organic ligand represented by formula (2), (3), or (4), and X is an hydroxide ion, halide ion, or nitrate ion.

11. The process of claim 10, wherein the organotin compound is at least one member selected from $C_4H_9SnO(CH_3COCHCOCH_3)$, $CH_3Sn(O)(OCOC_7H_{15})$, $(C_4H_9)_2Sn(OH)(CH_3COCHCOOC_3H_7)$, $(C_4H_9)_2Sn(OH)(OCOC_7H_{15})$, $C_4H_9Sn(OH)(CH_3COCHCOCH_3)_2$, $CH_3Sn(OH)(OCOC_7H_{15})_2$, $(C_4H_9)_2SnCl(CH_3COCHCOCOOC_3H_7)$, $(C_4H_9)_2Sn(NO_3)(OCOC_7H_{15})$, $(CH_3)_2Sn(OH)(NO_3)$, $C_4H_9Sn(NO_3)(CH_3COCHCOC_7H_{15})_2$, $(CH_3)_3Sn(CH_3COCHCOCH_3)$, $(CH_3)_2Sn(OCOCH=CHCOO)$, $(C_4H_9)_2Sn(OCOCH=CHCOOC_2H_5)_2$, and $(CH_3)_3SnSn(CH_3)_3$.

12. The process of claim 11, wherein $C_4H_9Sn(O)(CH_3COCHCOCH_3)$ has been prepared by reacting $C_4H_9Sn(O)(OH)$ with $CH_3COCH_2COCH_3$.

13. The process of claim 11, wherein $CH_3Sn(O)(OCOC_3H_{15})$ has been prepared by reacting $CH_3Sn(O)(OH)$ with $C_7H_{15}COOH$.

14. The process of claim 11, wherein $(C_4H_9)_2Sn(OH)(CH_3COCHCOOC_3H_7)$ has been prepared by reacting $(C_4H_9)_2Sn(O)$ with $CH_3COCH_2COOC_3H_7$.

15. The process of claim 11, wherein $(CH_3)_2Sn(OH)(OCOC_3H_7)$ has been prepared by reacting $(CH_3)_2Sn(O)$ with $C_3H_7COOH$.

16. The process of claim 11, wherein $C_4H_9Sn(OH)(CH_3COCHCOCH_3)_2$ has been prepared by reacting $C_4H_9Sn(O)(OH)$ with $CH_3COCH_2COCH_3$.

17. The process of claim 11, wherein $CH_3Sn(OH)(OCOC_7H_{15})$ has been prepared by reacting $CH_3Sn(O)(OH)$ with $C_7H_{15}COOH$.

18. The process of claim 1, wherein the mixing ratio of at least one member selected from the organic-ligand-containing metal complex compounds and the hydrolytic condensation products thereof to the at least one organotin compound is in the range of from 1:0.05 to 1:3.0 by mole.

19. The process of claim 1, wherein the mixing ratio of the sum of (a) at least one member selected from the organic-ligand-containing metal complex compounds and the hydrolytic condensation products thereof and (b) the at least one organotin compound to (c) the solvent is in the range of from 5:95 to 50:50 by weight.

20. The process of claim 19, wherein mixing proportions of the solvent are 60 to 80% by weight.

21. The process of claim 1, wherein the solvent dissolves the organic-ligand-containing metal complex compound, the hydrolytic condensation product, and the organotin compound.

22. The process of claim 21, wherein the solvent is an alcohol, an ethylene glycol monoalkyl ether, or a mixture of these compounds.

23. The process of claim 1, wherein the application of the composition is carried out by any of spinner coating, roll coating, dipping, spray, and screen printing.

24. The process of claim 1, wherein the Ag paste contains an Ag powder as the main component and a powder of Ti, Mg, or Ni and a borosilicate glass frit, as auxiliary components.

25. The process of claim 22, wherein the alcohol is selected from the group consisting of ethanol and isopropanol.

26. A process for producing solar cells, which comprises applying a composition for anti-reflection coating formation on one side of a silicon substrate which has a p-n junction therein, printing an Ag paste for contact formation on predetermined areas of the coating, and heat-treating the resulting plate at a temperature of 400° to 900° C. to complete an anti-reflection coating and a light-receiving side contact, the composition for anti-reflection coating formation containing as essential components, (a) at least one member selected from the group consisting of organic-ligand-containing metal complex compounds represented by the general formula $M(OR_1)_n(L)_{a-n}$     (5)

wherein M is a metal selected from Zn, Al, Ga, In, Ti, Zr, Sn, V, Nb, Ta, Mo and W; $OR_1$ is an alkoxy group; $R_1$ is a $C_1$–$C_{18}$ alkyl group; L is an organic ligand which forms a non-hydrolyzable bond with the metal ion; a is the valency of the metal M; and n is an integer satisfying $1 \leq n < a$, and hydrolytic condensation products of the compounds of formula (5), said products being represented by the general formula $$(OR_1)_{n-1}M(L)_{a-n}O-M(OR_1)_{n-1}(L)_{a-n} \qquad (6)$$

where M, $OR_1$, L, a, and n are as defined above;

(b) at least one organotin compound, the organotin compound being at least one member selected from the compounds represented by the general formula $(R_6)Sn(O)(OH)$ $(R_6)_2Sn(O)$ $(R_6)_3Sn(L)$ $(R_6)_3SnX$ $(R_6)_2Sn(L)_2$ or $(R_6)_3SnSn(R_6)_3$ wherein $R_6$ is a $C_1$–$C_{18}$ alkyl group, L is an organic ligand represented by formula (2), (3) or (4), and X is an hydroxide ion, halide ion, or nitrate ion; and
(c) a solvent.

* * * * *